United States Patent
Hajati

(10) Patent No.: US 9,454,954 B2
(45) Date of Patent: Sep. 27, 2016

(54) ULTRA WIDE BANDWIDTH TRANSDUCER WITH DUAL ELECTRODE

(71) Applicant: Arman Hajati, Santa Clara, CA (US)

(72) Inventor: Arman Hajati, Santa Clara, CA (US)

(73) Assignee: FUJIFILM DIMATIX, INC., Lebanon, NH (US)

( * ) Notice: Subject to any disclaimer, the term of this patent is extended or adjusted under 35 U.S.C. 154(b) by 574 days.

(21) Appl. No.: 13/830,288

(22) Filed: Mar. 14, 2013

(65) Prior Publication Data

US 2013/0294201 A1    Nov. 7, 2013

Related U.S. Application Data

(60) Provisional application No. 61/641,200, filed on May 1, 2012.

(51) Int. Cl.
| | |
|---|---|
| *B06B 1/06* | (2006.01) |
| *G10K 11/00* | (2006.01) |
| *G10K 11/34* | (2006.01) |
| *H01L 41/047* | (2006.01) |
| *H01L 41/09* | (2006.01) |

(52) U.S. Cl.
CPC ........... *G10K 11/343* (2013.01); *B06B 1/0622* (2013.01); *B06B 1/0629* (2013.01); *B06B 1/0696* (2013.01); *H01L 41/047* (2013.01); *H01L 41/0475* (2013.01); *H01L 41/098* (2013.01)

(58) Field of Classification Search
USPC .......................................................... 367/88
See application file for complete search history.

(56) References Cited

U.S. PATENT DOCUMENTS

| | | | |
|---|---|---|---|
| 4,398,116 A | 8/1983 | Lewis | |
| 5,115,810 A | 5/1992 | Watanabe et al. | |
| 5,969,621 A | 10/1999 | Getman et al. | |
| 6,262,946 B1 | 7/2001 | Khuri-Yakub et al. | |
| 7,477,572 B2 | 1/2009 | Caronti et al. | |
| 7,646,133 B2 | 1/2010 | Degertekin | |
| 7,652,410 B2 | 1/2010 | Prus | |
| 7,728,487 B2 * | 6/2010 | Adachi | A61B 8/4483 310/309 |
| 7,902,722 B2 | 3/2011 | Vilkomerson | |

(Continued)

FOREIGN PATENT DOCUMENTS

| | | |
|---|---|---|
| CN | 101084586 | 12/2007 |
| CN | 101262960 | 9/2008 |

(Continued)

OTHER PUBLICATIONS

"PCT, International Search Report and Written Opinion of the International Searching Authority for International Application No. PCT/US2013/037379", (Dec. 13, 2013), Whole Document.

(Continued)

*Primary Examiner* — James Hulka
(74) *Attorney, Agent, or Firm* — Blakely, Sokoloff, Taylor & Zafman LLP

(57) ABSTRACT

Wide bandwidth piezoelectric micromachined ultrasonic transducers (pMUTs), pMUT arrays and systems having wide bandwidth pMUT arrays are described herein. For example, a piezoelectric micromachined ultrasonic transducer (pMUT) includes a piezoelectric membrane disposed on a substrate. A reference electrode is coupled to the membrane. First and second drive/sense electrodes are coupled to the membrane to drive or sense a first and second mode of vibration in the membrane.

16 Claims, 10 Drawing Sheets

(56) References Cited

U.S. PATENT DOCUMENTS

| | | | | |
|---|---|---|---|---|
| 7,982,362 | B2* | 7/2011 | Adachi | A61B 8/4483 310/309 |
| 8,327,711 | B2* | 12/2012 | Kasai | H04R 19/005 73/649 |
| 8,861,753 | B2* | 10/2014 | Kasai | H04R 19/016 381/162 |
| 9,070,861 | B2* | 6/2015 | Bibl | B06B 1/0644 |
| 9,070,862 | B2* | 6/2015 | Bibl | B06B 1/0644 |
| 9,074,985 | B2* | 7/2015 | Lebental | G01N 15/088 |
| 2002/0115198 | A1* | 8/2002 | Nerenberg | B06B 1/0292 435/287.2 |
| 2003/0137224 | A1 | 7/2003 | Zloter et al. | |
| 2004/0174773 | A1 | 9/2004 | Thomenius et al. | |
| 2004/0190377 | A1 | 9/2004 | Lewandowski et al. | |
| 2005/0203397 | A1 | 9/2005 | Degertekin | |
| 2007/0059858 | A1 | 3/2007 | Caronti et al. | |
| 2007/0164631 | A1 | 7/2007 | Adachi et al. | |
| 2007/0193354 | A1 | 8/2007 | Felix et al. | |
| 2008/0013405 | A1 | 1/2008 | Moon et al. | |
| 2009/0001853 | A1* | 1/2009 | Adachi | A61B 8/4483 310/323.19 |
| 2009/0161490 | A1 | 6/2009 | Wall et al. | |
| 2009/0163129 | A1 | 6/2009 | Durjan et al. | |
| 2009/0182237 | A1 | 7/2009 | Angelsen et al. | |
| 2009/0204001 | A1 | 8/2009 | Ona et al. | |
| 2009/0301200 | A1 | 12/2009 | Tanaka et al. | |
| 2010/0168583 | A1 | 7/2010 | Dausch et al. | |
| 2010/0174195 | A1 | 7/2010 | Haider et al. | |
| 2010/0201222 | A1* | 8/2010 | Adachi | A61B 8/4483 310/317 |
| 2010/0212432 | A1* | 8/2010 | Kasai | H04R 19/005 73/654 |
| 2010/0268058 | A1 | 10/2010 | Chen | |
| 2010/0277040 | A1 | 11/2010 | Klee et al. | |
| 2010/0327695 | A1 | 12/2010 | Goel et al. | |
| 2011/0057541 | A1 | 3/2011 | Cho et al. | |
| 2011/0074248 | A1 | 3/2011 | Hishinuma | |
| 2011/0272693 | A1* | 11/2011 | Kobayashi | B06B 1/0292 257/48 |
| 2012/0086307 | A1* | 4/2012 | Kandori | H02N 1/006 310/300 |
| 2012/0176002 | A1 | 7/2012 | Kim et al. | |
| 2012/0206014 | A1* | 8/2012 | Bibl | B06B 1/0644 310/331 |
| 2013/0070942 | A1* | 3/2013 | Kasai | H04R 3/00 381/162 |
| 2013/0294622 | A1* | 11/2013 | Kasai | H04R 19/005 381/162 |
| 2014/0117812 | A1* | 5/2014 | Hajati | B06B 1/0276 310/314 |

FOREIGN PATENT DOCUMENTS

| | | |
|---|---|---|
| CN | 101583062 | 11/2009 |
| CN | 201993187 | 9/2011 |
| CN | 102305627 | 1/2012 |
| CN | 102595287 | 7/2012 |
| EP | 1764162 | 3/2007 |
| EP | 2110186 | 10/2009 |
| EP | 2130495 | 12/2009 |
| JP | 2009260723 | 11/2009 |
| WO | WO-0225630 | 3/2002 |
| WO | WO-2004016036 | 2/2004 |
| WO | WO-2007013814 | 1/2007 |
| WO | WO-2011094393 | 8/2011 |

OTHER PUBLICATIONS

"PCT, International Search Report and Written Opinion of the International Searching Authority for International Application No. PCT/US2013/037382", (Feb. 4, 2014), Whole Document.

"PCT, International Search Report and Written Opinion of the International Searching Authority for International Application No. PCT/US2013/037419", (Mar. 28, 2014), Whole Document.

"Non Final Office Action for U.S. Appl. No. 13/835,500", (Sep. 26, 2013), Whole Document.

"Office Action for U.S. Appl. No. 13/648,225", (Oct. 24, 2014), Whole Document.

"PCT, Preliminary Report on Patentability (Chapter I of the Patent Cooperation Treaty) for International Application No. PCT/US2013/037379", (Nov. 13, 2014), Whole Document.

"PCT, Preliminary Report on Patentability (Chapter I of the Patent Cooperation Treaty) for International Application No. PCT/US2013/037382", (Nov. 13, 2014), Whole Document.

"PCT, Preliminary Report on Patentability (Chapter I of the Patent Cooperation Treaty) for International Application No. PCT/US2013/037419", (Nov. 13, 2014), Whole Document.

First Office Action for Chinese Patent Application No. 201380023320.2 mailed Jan. 29, 2016, 21 pgs.

First Office Action for Chinese Patent Application No. 201380023381.9 mailed Dec. 23, 2015, 7 pgs.

International Search Report and Written Opinion from PCT/US2013/63255 mailed Feb. 7, 2014, 18 pgs.

International Preliminary Report on Patentability from PCT/US2013/063255 mailed May 7, 2015, 8 pgs.

Non-Final Office Action from U.S. Appl. No. 13/830,251 mailed Jul. 16, 2015, 16 pgs.

Final Office Action from U.S. Appl. No. 13/830,251 mailed Dec. 31, 2015, 12 pgs.

Notice of Allowance for U.S. Appl. No. 13/835,500 mailed Feb. 18, 2015, 7 pgs.

Office Action for Chinese Patent Application No. 201380023369.8 mailed Feb. 22, 2016, 21 pages.

Notice of Allowance for U.S. Appl. No. 13/835,500, (Feb. 18, 2013), Whole Document.

Notice of Allowance for U.S. Appl. No. 13/835,500, (May 7, 2014), Whole Document.

Extended European Search Report and Written Opinion from EP Patent Application No. 13848357.3 mailed May 27, 2016, 9 pgs.

* cited by examiner

ULTRA WIDE BANDWIDTH TRANSDUCER WITH DUAL ELECTRODE

CROSS-REFERENCE TO RELATED APPLICATIONS

This application claims priority to the U.S. provisional utility patent application titled "ULTRA WIDE BANDWIDTH TRANSDUCER WITH DUAL ELECTRODE," filed on May 1, 2012 and having application No. 61/641,200, the entire contents of which are incorporated herein by reference for all purposes.

TECHNICAL FIELD

Embodiments of the invention generally relate to piezoelectric transducers, and more specifically pertain to ultra wide bandwidth transducers with dual electrodes.

BACKGROUND

An ultrasonic piezoelectric transducer device typically includes a piezoelectric membrane capable of vibrating in response to a time-varying driving voltage to generate a high frequency pressure wave in a propagation medium (e.g., air, water, or body tissue) in contact with an exposed outer surface of the transducer element. This high frequency pressure wave can propagate into other media. The same piezoelectric membrane can also receive reflected pressure waves from the propagation media, and convert the received pressure waves into electrical signals. The electrical signals can be processed in conjunction with the driving voltage signals to obtain information on variations of density or elastic modulus in the propagation media.

While many ultrasonic transducer devices that use piezoelectric membranes are formed by mechanically dicing a bulk piezoelectric material or by injection molding a carrier material infused with piezoelectric ceramic crystals, devises can be advantageously fabricated inexpensively to exceedingly high dimensional tolerances using various micromachining techniques (e.g., material deposition, lithographic patterning, feature formation by etching, etc.). As such, large arrays of transducer elements are employed with individual ones of the arrays driven via beam forming algorithms. Such arrayed devices are known as pMUT arrays.

One issue with conventional pMUT arrays is that the bandwidth, being a function of damping implemented by a backing layer, may be limited. Because ultrasonic transducer applications, such as fetal heart monitoring and arterial monitoring, span a wide range of frequencies (e.g., lower frequencies providing relatively deeper imaging capability and higher frequencies providing shallower imaging capability), axial (i.e. range) resolution would be advantageously improved by enhancing the bandwidth of a pMUT array for a given level of dampening through a backing layer.

SUMMARY

Wide bandwidth piezoelectric micromachined ultrasonic transducers (pMUTs), pMUT arrays and systems having wide bandwidth pMUT arrays are described herein.

In an embodiment, a pMUT includes a piezoelectric membrane disposed on a substrate. A reference electrode held at a reference voltage potential is coupled to the membrane. First and second drive/sense electrodes are coupled to the membrane to drive and/or sense a first and second mode of vibration in the membrane.

In another embodiment, an apparatus for generating and sensing pressure waves in a medium includes a pMUT having a piezoelectric membrane disposed on a substrate. A reference electrode is coupled to the membrane. First and second drive/sense electrodes are coupled to the membrane to drive and/or sense first and second modes of vibration in the membrane. A first signal generator is coupled to the first drive/sense electrode and provided to drive a first electrical signal on the first drive/sense electrode relative to the reference electrode. A second signal generator is coupled to the second drive/sense electrode and provided to drive a second electrical signal on the second drive/sense electrode relative to the reference electrode.

In another embodiment, a pMUT array includes a plurality of sets of electrode rails disposed over an area of a substrate. Each set of electrode rails includes a reference rail and a pair of independently electrically addressable drive/sense rails. The pMUT array also includes a plurality of piezoelectric transducer elements having separate element populations. Each element population has more than one transducer element coupled to one of the sets of electrode rails. Each of the piezoelectric transducer elements further includes a piezoelectric membrane. The pMUT array also includes a reference electrode coupled to the membrane and the reference rail. First and second drive/sense electrodes are coupled to the membrane and to respective ones of the drive/sense electrode rail pair.

In another embodiment, a method of operating an apparatus for generating and sensing pressure waves in a medium with a pMUT includes generating a first electrical signal. A second electrical signal is also generated. At least one of amplitude and phase of one of first and second signals is modulated relative to the other. The first electrical signal is applied to the first drive/sense electrode of the pMUT and the second electrical signal to the second drive/sense electrode of the pMUT to control a relative strength of the first and second modes of vibration.

BRIEF DESCRIPTION OF THE DRAWINGS

Embodiments of the present invention are illustrated by way of example, and not by way of limitation, and can be more fully understood with reference to the following detailed description when considered in connection with the figures in which.

DETAILED DESCRIPTION

Figure 1A:
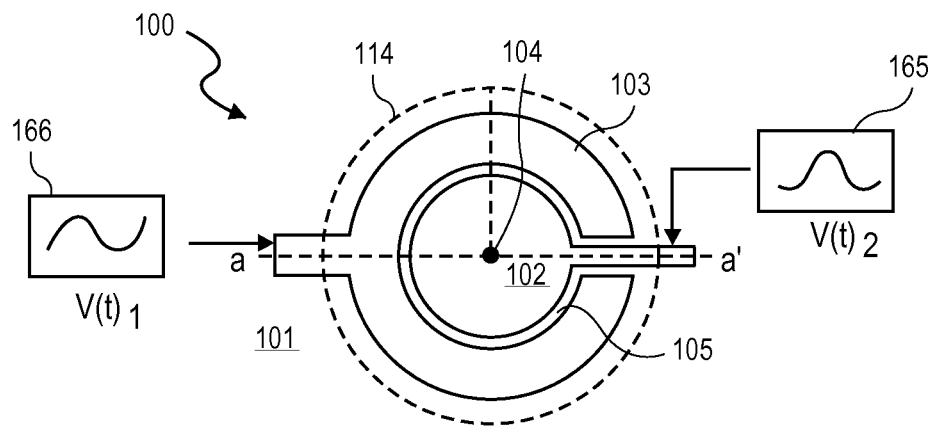
FIG. 1A is a plan view of a pMUT with a circular membrane, in accordance with an embodiment.

In the following description, numerous details are set forth. It will be apparent, however, to one skilled in the art, that the present invention may be practiced without these specific details. In some instances, well-known methods and devices are shown in block diagram form, rather than in detail, to avoid obscuring the present invention. Reference throughout this specification to "an embodiment" means that a particular feature, structure, function, or characteristic described in connection with the embodiment is included in at least one embodiment of the invention. Thus, the appearances of the phrase "in an embodiment" in various places throughout this specification are not necessarily referring to the same embodiment of the invention. Furthermore, the particular features, structures, functions, or characteristics may be combined in any suitable manner in one or more embodiments. For example, a first embodiment may be combined with a second embodiment anywhere the two embodiments are not mutually exclusive.

Unless specifically stated otherwise, terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

The terms "coupled" and "connected," along with their derivatives, may be used herein to describe structural relationships between components. It should be understood that these terms are not intended as synonyms for each other. Rather, in particular embodiments, "connected" may be used to indicate that two or more elements are in direct physical or electrical contact with each other. "Coupled" may be used to indicated that two or more elements are in either direct or indirect (with other intervening elements between them) physical or electrical contact with each other, and/or that the two or more elements co-operate or interact with each other (e.g., as in a cause an effect relationship).

The terms "over," "under," "between," and "on" as used herein refer to a relative position of one component or material layer with respect to other components or layers where such physical relationships are noteworthy for mechanical components in the context of an assembly, or in the context of material layers of a micromachined stack. One layer (component) disposed over or under another layer (component) may be directly in contact with the other layer (component) or may have one or more intervening layers (components). Moreover, one layer (component) disposed between two layers (components) may be directly in contact with the two layers (components) or may have one or more intervening layers (components). In contrast, a first layer (component) "on" a second layer (component) is in direct contact with that second layer (component).

Conventional piezoelectric transducer designs typically include electrodes that cover an entire membrane of the transducer. The electrode is used to excite the first mode of vibration of the membrane to generate an ultrasound wave. By contrast, in accordance with one or more embodiments of the present invention, a pair of drive/sense electrodes are employed. Each of the pair of drive/sense electrodes is coupled to a separate, independent, electrode rail or bus and may therefore be driven to independent electrical potentials by separate drive signals having selectable amplitudes relative to the reference electrode and with a selectable phase between the two drive signals. In one such embodiment, this arrangement enables exploitation of both first and second modes of vibration. By rendering both the first and second modes accessible, improved signal processing capabilities may be achieved on a receiving mode of the transducer.

As described in greater detail below, in an embodiment, a transducer membrane is excited by two drive/sense electrodes, for example, an inner circular solid electrode and a circumferential annular electrode. By changing the amplitude and the phase of the inputs to these electrodes, e.g., beamforming, the relative strength of the first and second mode shapes may be controlled. Furthermore, the interactions of the first and second modes may also be controlled. In an embodiment, such a beamforming approach is applied to the output signals in the receiving mode to provide both low frequency and high frequency components. The signal processing capability achieved with dual drive/sense electrode channels may greatly improve an image quality derived there from.

In an embodiment, by using both first and second modes shapes, a greater than 100% fractional bandwidth is achieved using an optimized ultra wide bandwidth (UWB) design, as described in greater detail below. In an embodiment, by employing a second mode shape with higher resonance frequency, high frequency transducers may have a relatively larger size (e.g., diameter) piezoelectric membrane than what would be necessary to achieve a comparable frequency with the first mode shape (e.g., lower frequency resonance). The use of a larger piezoelectric membrane may enable improved sensitivity for a transducer employing the membrane. Also, fabrication of the transducer may be more straightforward, or may the transducer be made more reliable, if incorporating a relatively larger piezoelectric membrane. In one such embodiment, high frequency operation of a larger piezoelectric membrane enables use of the transducer, or an array thereof, in high frequency intravenous ultra-sonic (HF IVUS) devices operating at over approximately 20 MHz, e.g., in a range of approximately 40-60 MHz.

FIG. 1A illustrates a top-down view of a pMUT 100, in accordance with an embodiment. The pMUT 100 includes a piezoelectric membrane 114 disposed on a substrate 101. First and second drive/sense electrodes 102 and 103 are coupled to the membrane 114. First and second drive/sense electrodes 102 and 103 are provided to drive or sense a first and second mode of vibration in the membrane 114, as described below in greater detail in association with FIGS. 3 and 4. Although not shown in FIG. 1A, a reference electrode is coupled to the membrane 114, as described in greater detail below in the context of FIGS. 2A-2C.

In the exemplary embodiment depicted in FIG. 1A, the piezoelectric membrane 114 has a circular or spheroidal geometry. In one such embodiment, the first drive/sense electrode 102 has a circular or spheroidal geometry with a diameter smaller than that of the membrane 114 and with a center 104 aligned to a center of the membrane 114, as depicted in FIG. 1A. In one such embodiment, the second drive/sense electrode 103 has an annular geometry with a center aligned to the center of the membrane 114, with an outer diameter that may be smaller or larger than that of the membrane 114 and with an inner diameter that is greater than an outer diameter of the first drive/sense electrode 102 to circumscribe at least a portion of the first drive electrode 102 with a spacing 105 there between.

In an embodiment, the membrane 114 is circular, the first and second drive/sense electrodes 102 and 103 are co-planar and disposed on a first side of the piezoelectric membrane 114. In one such embodiment, the reference electrode is disposed on an opposite side of the piezoelectric membrane 114 with the second drive/sense electrode 103 having a discontinuity through which a first lead 165 coupled to the first drive/sense electrode 102 is routed. In an embodiment, a second lead 166 is coupled to the second drive/sense electrode 103. In an embodiment, lead 165 includes, or is coupled to, a first signal generator that is to drive a first electrical signal on the first drive/sense electrode 102 relative to the reference electrode, as described in greater detail in association with FIGS. 3A and 3B. Lead 166 includes, or is coupled to, a second signal generator that is to drive a second electrical signal on the second drive/sense electrode 103 relative to the reference electrode, as is described in greater detail in association with FIGS. 3A and 3B.

Figure 1B:
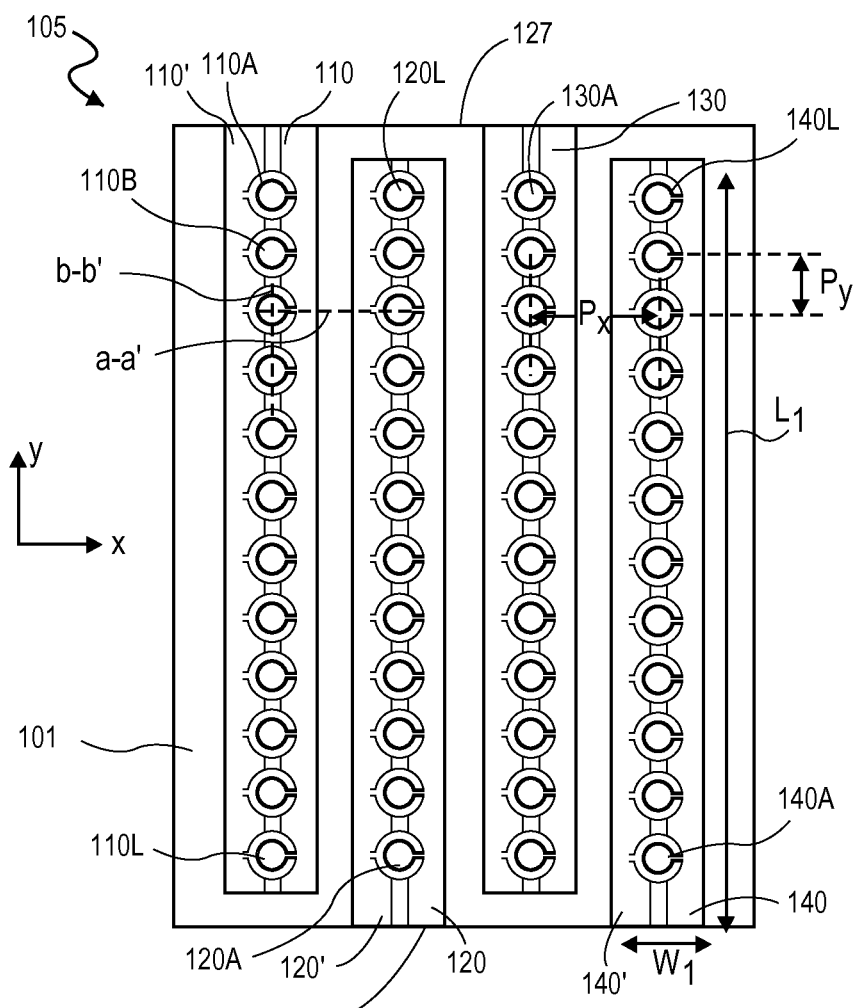
FIG. 1B is a plan view of a pMUT array with transducer elements, in accordance with an embodiment.
Figure 1C:
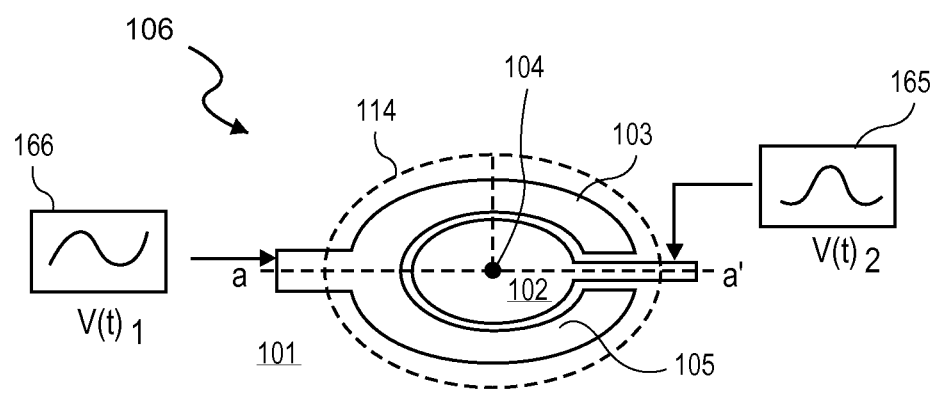
FIG. 1C s a plan view of a pMUT with an elliptical membrane, in accordance with an embodiment.

In another embodiment depicted in FIG. 1C, the element 106 employs an elliptical membrane. Elliptical membrane embodiments (or ellipsoidal embodiments where the membrane has a non-planar resting state as described elsewhere herein) potentially offer a greater fill factor and may be more readily stimulated into higher modes (second, third, etc.) of resonance by multiple drive electrodes. For elliptical embodiments, the first drive/sense electrode 103 is again split with the second drive/sense electrode 102 routed into a central portion of the elliptical membrane, substantially as for the circular embodiment. The perimeter shape of the drive electrodes 102, 103 may also have elliptical forms, to match the membrane form in the same manner circular electrodes follow the circular membrane form.

Figure 2A:
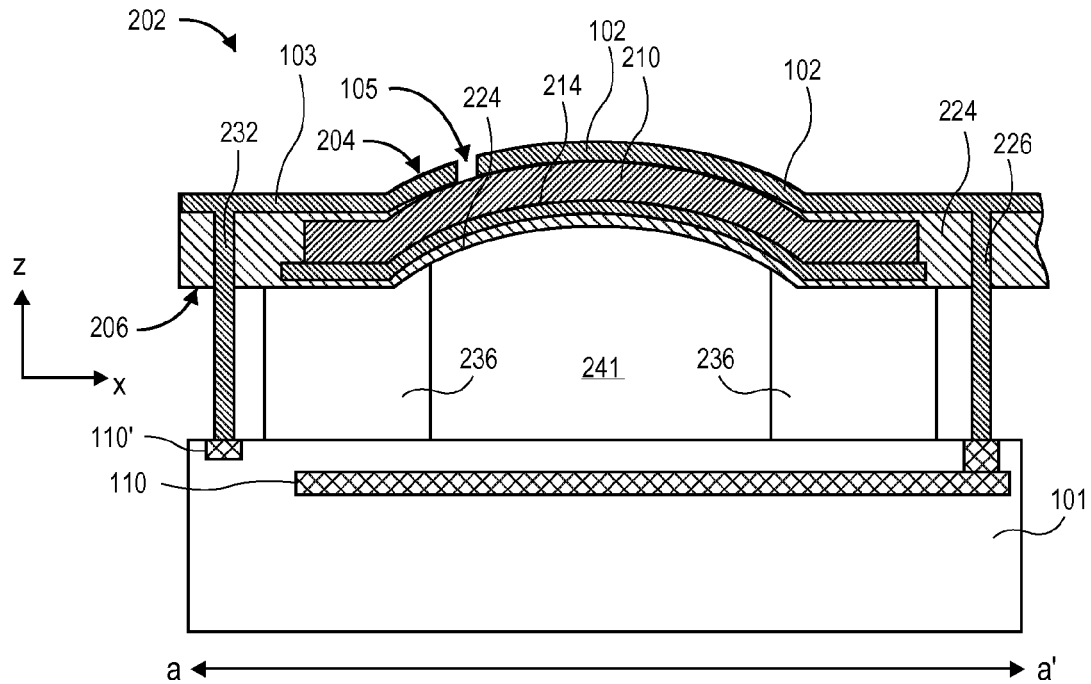
FIGS. 2A, 2B, and 2C are cross-sectional views of a transducer element which is utilized in the pMUT array of FIG. 1B, in accordance with embodiments.
Figure 2B:
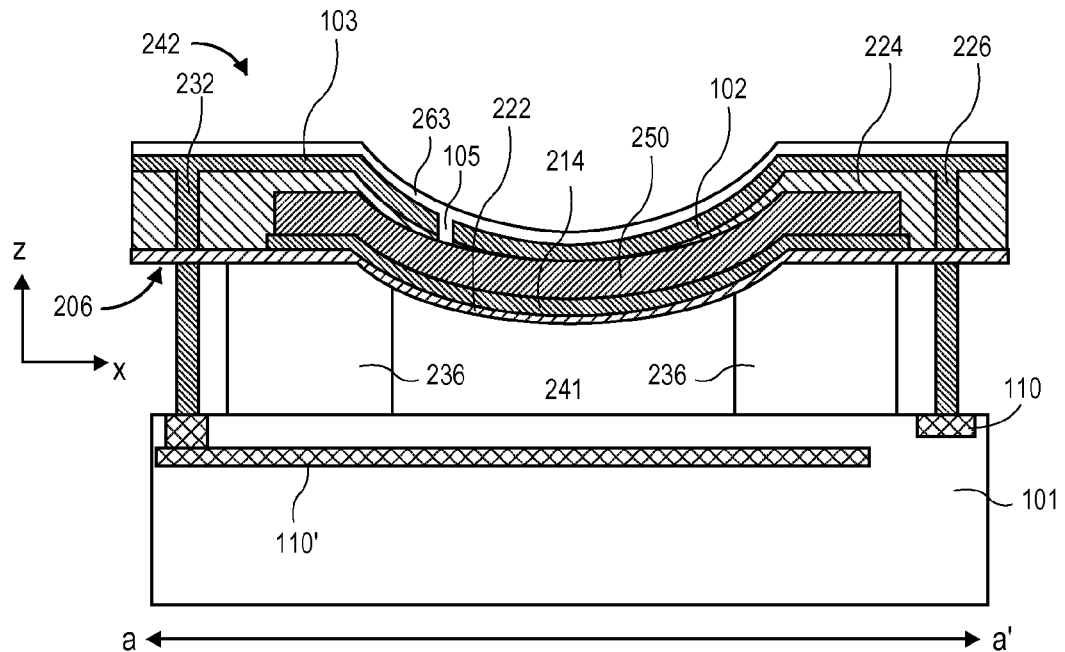
Figure 2C:
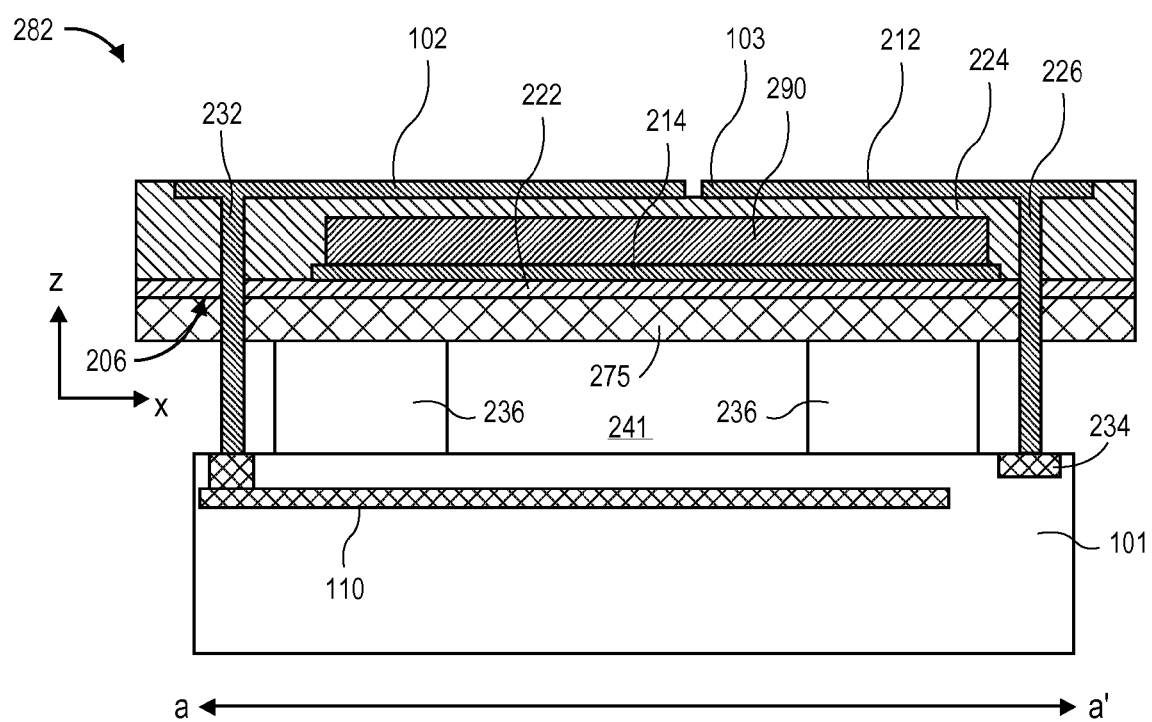

FIG. 1B is a plan view of a pMUT array 105, in accordance with an embodiment. FIGS. 2A, 2B, and 2C are cross-sectional views of transducer element embodiments, any of which may be representative of the pMUT 100 and further utilized in the pMUT array 105, in accordance with embodiments.

The array 105 includes a plurality of first electrode rails 110, 120, 130, 140 and corresponding second electrode rails 110', 120', 130', 140', respectively disposed over an area of a substrate 101 defined by a first dimension, x and a second dimension y. Each of the drive/sense electrode rail pairs (e.g., pair 110,110') is electrically addressable independently from any other drive/sense electrode rails (e.g., from each other and from pairs 120,120' or 130,103'). The drive/sense electrode rail pair (e.g., 110,110') and reference (e.g., ground) electrode rail are depicted in the cross-sectional views of FIG. 2A-2C. In FIG. 1B, the drive/sense electrode rail pair 110,110' and drive/sense electrode rail pair 120,120' represent a repeating cell in the array. For example, with the first drive/sense electrode rail pair 110,110' coupled to a first end 127 and the adjacent drive/sense electrode rail pair 120,120' coupled a second end 128 to form a interdigitated finger structure. The drive/sense electrode rail pair 130,130' and drive/sense electrode rail pair 140,140' repeat the interdigitated structure with additional cells forming a 1D electrode array of arbitrary size (e.g., 128 rail pairs, 256 rail pairs, etc.).

In an embodiment, a pMUT array includes a plurality of piezoelectric transducer element populations. Each piezoelectric transducer element population is to operate in concert with a frequency response that is a composite of the individual transducer elements within each element population. In an embodiment, within a given element population, each transducer element's drive/sense electrode is electrically coupled in parallel to one drive/sense electrode rail of a rail pair so that all first drive/sense electrodes are at a same electrical potential and, likewise, all second drive/sense electrodes are at a same electrical potential. For example in FIG. 1B, transducer elements 110A, 110B, . . . 110L have drive/sense electrode pairs coupled to the drive/sense electrode rail pair 110,110'. Similarly, first and second drive/sense electrodes of the transducer elements 120A-120L are all coupled in parallel to the drive/sense electrode rail pair 120,120', respectively. Generally, any number of piezoelectric transducer elements may be lumped together, as a function of the array size and element pitch. In the embodiment depicted in FIG. 1B, each piezoelectric transducer element population (e.g., 110A-110L) is disposed over a length $L_1$ of the substrate that is at least five times, and preferably at least an order of magnitude, larger than a width $W_1$ of the substrate. Other geometries over which an element population is arrayed are also possible with the guiding principle being that each element population in the pMUT array is to have a known spatial relationship within the array such that beam forming techniques can be applied at the population level.

In embodiments, each piezoelectric transducer element includes a piezoelectric membrane. While the piezoelectric membrane may generally be of any shape conventional in the art, in exemplary embodiments the piezoelectric membrane has rotational symmetry. For example, in the pMUT array 105, each transducer element includes a piezoelectric membrane having a circular geometry. The piezoelectric membrane may further be a spheroid with curvature in a third (z) dimension to form a dome (as further illustrated by FIG. 2A), or a dimple (as further illustrated in FIG. 2B). Planar membranes are also possible, as further illustrated in FIG. 2C, where the transducer element is planar in a resting state.

Thus, in an embodiment, a pMUT array includes a plurality of sets of electrode rails disposed over an area of a substrate. Each set of electrode rails includes a reference rail and a pair of independently electrically addressable drive/sense rails. The pMUT array also includes a reference electrode rail coupled to the a reference electrode in each transducer element. Within the pMUT array is a plurality of piezoelectric transducer elements having separate element populations. In an embodiment, each element population has more than one transducer element coupled to one of the sets of electrode rails with first and second drive/sense electrodes coupling piezoelectric membranes to respective ones of the drive/sense rails.

FIGS. 2A-2C are cross-sectional views taken along the a-a' axis of FIG. 1B, showing exemplary micromachined (i.e., microelectromechanical) aspects of individual transducer elements. It is to be appreciated that the structures depicted in FIGS. 2A-2C are included primarily as context for particular aspects of the present invention and to further illustrate the broad applicability of the present invention with respect to piezoelectric transducer element structure.

In FIG. 2A, a convex transducer element 202 includes a top surface 204 that during operation forms a portion of a vibrating outer surface of the pMUT array 105. The transducer element 202 also includes a bottom surface 206 that is attached to a top surface of a substrate 101. The transducer element 202 includes a convex or dome-shaped piezoelectric membrane 210 disposed between a reference electrode 214, a first drive/sense electrode 102 and a second drive/sense electrode 103. A spacing 105 separate the first drive/sense electrode 102 from the second drive/sense electrode 103. In one embodiment, the piezoelectric membrane 210 can be formed by depositing (e.g., sputtering) piezoelectric material particles in a uniform layer on a profile-transferring substrate (e.g., photoresist) that has a dome formed on a planar top surface, for example. An exemplary piezoelectric material is Lead Zirconate Titanate (PZT), although any known in the art to be amenable to conventional micromachine processing may also be utilized, such as, but not limited to doped polymethylmethacrylate (PMM) polymer particles, and aluminum nitride (AlN). The drive/sense electrodes 102 and 103 and reference electrode 214 can each be a thin film layer of conductive material deposited (e.g., by PVD, ALD, CVD, etc.) on the profile-profile transferring substrate. The conductive materials for the drive electrode layer can be any known in the art for such function, such as, but not limited to, one or more of Au, Pt, Ni, Ir, etc.), alloys thereof (e.g., AuSn, IrITiW, AuTiW, AuNi, etc.), oxides thereof (e.g., $IrO_2$, $NiO_2$, $PtO_2$, etc.), or composite stacks of two or more such materials.

Further as shown in FIG. 2A, in some implementations, the transducer element 202 can optionally include a thin membrane layer 222, such as silicon dioxide that can serve as a support and/or etch stop during fabrication. A dielectric membrane 224 may further serve to insulate the drive/sense electrodes 102 and 103 from the reference electrode 214. Vertically-oriented electrical interconnect 226 connects the drive/sense electrode 102 to drive/sense circuits via the drive/sense electrode rail 110. A similar interconnect 232 connects the drive/sense electrode 103 to a rail 110'. Although not depicted, reference electrode 214 may be coupled to an independent reference rail. An annular support 236, having a hole 241 with an axis of symmetry vertically aligned with that of the transducer element 202, mechanically couples the piezoelectric membrane 210 to the substrate 101. The support 236 may be of any conventional material, such as, but not limited to, silicon dioxide, polycrystalline silicon, polycrystalline germanium, SiGe, and the like. Exemplary thicknesses of support 236 range from 10-50 μm and exemplary thickness of the membrane 224 range from 5-15 μm.

FIG. 2B shows another exemplary configuration for a transducer element 242 in which structures functionally similar to those in transducer element 202 are identified with like reference numbers. The transducer element 242 illustrates a concave piezoelectric membrane 250 that is concave in a resting state. Here, the reference electrode 214 is disposed below the bottom surface of the concave piezoelectric membrane 250, while the drive/sense electrodes 102 and 103 are disposed above the top surface.

FIG. 2C shows another exemplary configuration for a transducer element 282 in which structures functionally similar to those in transducer element 202 are identified with like reference numbers. The transducer element 262 illustrates a planar piezoelectric membrane 290 that is planar in a resting state, and unlike the elements 202, 242, operates in bending mode and therefore further employs a membrane 275 (typically of silicon). Here, the reference electrode 214 is disposed below the bottom surface of the planar piezoelectric membrane 290, while the drive/sense electrodes 102 and 103 are disposed above the top surface. An opposite electrode configuration from that depicted in each of FIGS. 2A-2C is of course also possible.

Figure 3A:
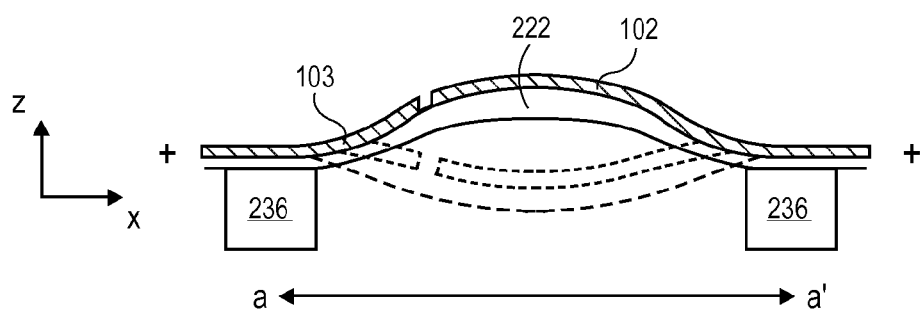
FIG. 3A depicts, in operation, a cross-sectional view of an apparatus similar to apparatus of FIG. 1A taken along the a-a' axis, in accordance with an embodiment.
Figure 3B:
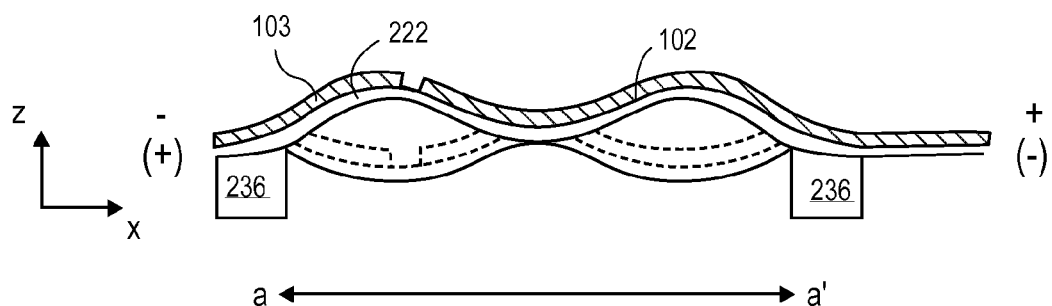
FIG. 3B depicts, in operation, a cross-sectional view of an apparatus similar to apparatus of FIG. 1A taken along the a-a' axis, in accordance with an embodiment.

In an embodiment, referring again to FIG. 1A as well as FIGS. 3A and 3B, during operation, the membrane 114 has a first mode of vibration with a first resonant frequency and a second mode of vibration with a second resonant frequency greater than that of the first resonant frequency. For example, FIG. 3A depicts, in operation, a cross-sectional view of an apparatus similar to apparatus 100 taken along the a-a' axis, in accordance with an embodiment. A membrane 222 (which may be planar, domed, or a cavity in a resting state) is supported by supports 236 and driven by drive sense/electrode pair 102 and 103 to provide a first mode of vibration when the drive sense/electrode pair 102 and 103 has an in-phase time varying voltage applied thereto (e.g., +voltage to both electrodes 102 and 103, etc.). FIG. 3B depicts, in operation, a cross-sectional view of an apparatus similar to apparatus 100 taken along the a-a' axis, in accordance with another embodiment. A membrane 222 (which may be planar, domed, or a cavity in a resting state) is supported by supports 236 and driven by drive sense/ electrode pair 102 and 103 to provide a second mode of vibration when the drive sense/electrode pair 102 and 103 has an out-of-phase time varying voltage waveform applied thereto (e.g., +voltage is applied to one of the electrodes 102 and 103 while a −voltage is applied to the other of electrodes 102 and 103, etc.). Because the second mode of vibration is of a higher frequency (e.g., 2×) the fundamental, or first, mode of vibration, larger membrane sizes may be utilized to reach high frequency regimes. For example, in a specific embodiment where the membrane 222 diameter is larger than 2 μm, a first mode of vibration has a first resonant frequency of at least 15 MHz, and the second mode of vibration has a second resonant frequency greater than that of the first resonant frequency, such as 30-60 MHz.

Figure 4A:
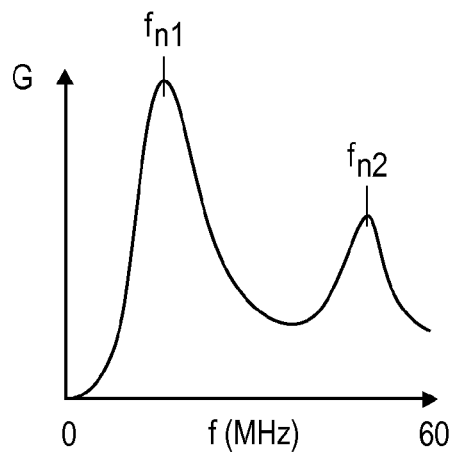
FIGS. 4A and 4B are plots of performance metrics for the PMUTs of FIGS. 3A and 3B, in accordance with embodiments.
Figure 4B:
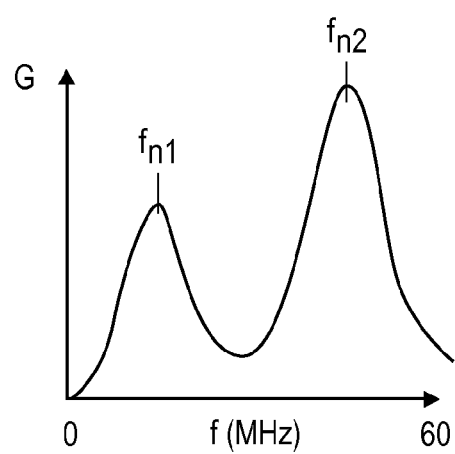

FIGS. 4A and 4B are plots of performance metrics for the PMUTs of FIGS. 3A and 3B, in accordance with embodiments. Referring to FIG. 4A, in one embodiment, the first and second signal generators (e.g., generators 166,165 from FIG. 1A, with output drive signal phases represented by bias polarity signs in FIGS. 3A and 3B) are to drive the first and second electrical signals to excite a first resonant mode ($f_{n1}$) of the membrane 114 or 222 more than a second resonant mode ($f_{n2}$) depending on the relative drive voltage magnitude and phase delay of the two applied drive signals. Referring to FIG. 4B, in another embodiment, the first and second signal generators are to drive the first and second electrical signals to excite the second resonant mode ($f_{n2}$) of the membrane 114 or 222 more than the first resonant mode ($f_{n1}$), depending on the relative drive voltage magnitude and phase delay of the two applied drive signals.

In an embodiment, a transducer apparatus further includes a signal processor coupled to the first and second drive electrodes. The signal processor is provided to receive both a low frequency component and a high frequency component of a response spectrum generated by the membrane vibrating in the first and second modes. A combination of responses associated with each of the first and second modes of vibration may be balanced as desired, including, in an embodiment, to be approximately equal in intensity strength, by varying the relative drive voltage magnitude and phase delay of the two applied drive signals.

In embodiments, a piezoelectric transducer element population includes a plurality of piezoelectric membranes of differing nominal size to provide a plurality of separate resonant frequencies. Spectral response may be shaped by integrating n different sizes (e.g., membrane diameters for the exemplary circular or spheriodal membranes described elsewhere herein) so as to provide for wide bandwidth. Unlike bulk PZT transducers, the resonance frequency of a pMUT can be readily tuned by geometry through lithography. As such, high-Q membranes of differing sizes may be integrated with different frequency responses to reach a high total bandwidth response from a given element population. In further embodiments, each transducer element population includes an identical set of transducer element sizes so that the spectral response from each population is approximately the same.

Figure 5A:
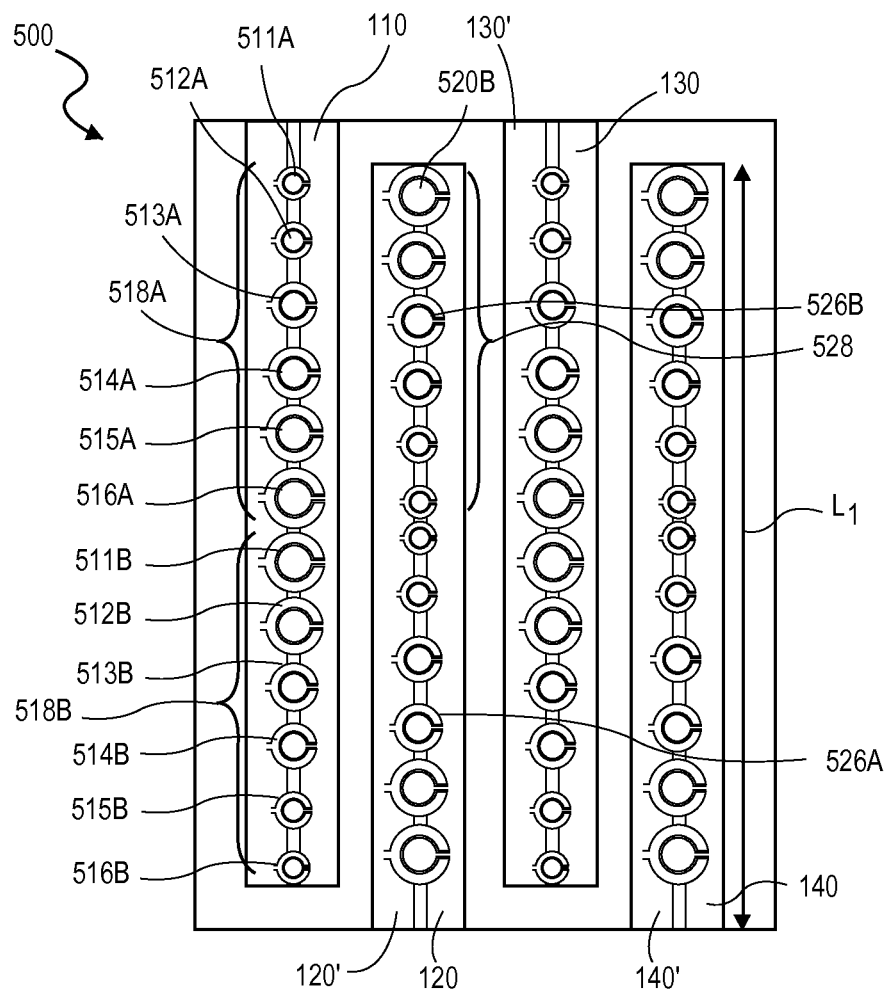
FIG. 5A is a plan view of a pMUT array with transducer elements of differing sizes, in accordance with an embodiment.

FIG. 5A is a plan view of a pMUT array 500 with transducer elements of differing sizes, in accordance with an embodiment. The pMUT array 500 has a similar layout as the pMUT array 100, with drive/sense electrode rail pairs 110,110' and 120,120' being parallel, but extending in opposite directions (e.g., from separate buses or interfaces) so as to be interdigitated along the x-dimension (i.e., a 1D array). Electrically coupled to one drive/sense electrode pair (e.g., 110,110') are transducer elements having 2-20, or more, different membrane sizes (e.g., diameters). The range of diameters will generally depend on the desired frequency range as a function of membrane stiffness and mass. Increments between successively larger membranes may be a function of the range and number of differently sized membranes with less frequency overlap occurring for larger size increments. An increment size can be selected to ensure all transducer elements contribute to response curve maintaining a 3 dB bandwidth. As an example, the a range of 20-150 µm would be typical for MHz frequency responses from a transducer having the general structure described in the context of FIGS. 2A-2C and an increment of 1-10 µm would typically provide sufficient response overlap.

As the number of transducer element (e.g., membrane) sizes increases, the resolution at a particular center frequency can be expected to go down as the distance between elements of a same size decreases. For example, where piezoelectric membranes of each piezoelectric transducer element population are in single file (i.e., with centers aligned along a straight line), effective pitch of same-sized transducers along the length $L_1$ is reduced with each additional transducer size in the population. In further embodiments therefore, each piezoelectric transducer element population comprises more than one piezoelectric transducer element of each nominal membrane size. For the exemplary embodiment depicted in FIG. 5A, electrically coupled to drive/sense electrode rail pair 110,110' are: piezoelectric transducer elements 511A and 511B of a first size (e.g., smallest diameter membrane); elements 512A, 512B of a second size (e.g., next to smallest diameter membrane); elements 513A, 513B; elements 514A, 514B, elements 515A, 515B; and elements 516A, 516B for six different sizes of membrane. As shown, membranes of a same size (e.g., 511A and 511B) are spaced apart by at least one intervening element having a membrane of different size. As shown, the membrane size gradually increases and/or decreases in a step-wise manner through adjacent elements. Graduating membrane size over a distance of the array has been found to mitigate deconstructive phasing possible between first and second membranes of drastically differing size in close proximity to each other. In other words, where a population of membranes are of different sizes, it is advantageous to spatially arrange the population over the substrate so as to have the difference in size between two adjacent membranes be smaller than the difference in size between the largest and smallest membranes in the population.

As further shown in FIG. 5A, a transducer element subgroup 518A is repeated as 518B along the length of the substrate over which the element population is disposed. Each transducer element subgroup 518A, 518B includes one piezoelectric transducer element of each nominal membrane size. In this exemplary embodiment, a heuristic layout is such the element population coupled to the drive/sense rail pair 110,110' has transducer elements of a same size spaced apart by at least one intervening element of a different size, but are spaced apart by no more than a length of the substrate occupied by one element subgroup. This has the effect of improving the uniformity of signal. As further illustrated in FIG. 5A, the similar element subgroup 528A is shifted down the length of the drive sense electrode rail pair 120/120' relative to the element subgroup 518A so as to spread the various element sizes more uniformly over the substrate. This positional offset also helps reduce crosstalk between the adjacent element populations by ensuring elements of a same size are not nearest neighbors (e.g., 526A is approximately half way between elements 516A and 516B). The transducer element populations for rail pairs 110, 110' and 120, 120' includes a cell that is then repeated for rail pairs 130, 130' and 140, 140,' and etc. over an entire array field.

Figure 5B:
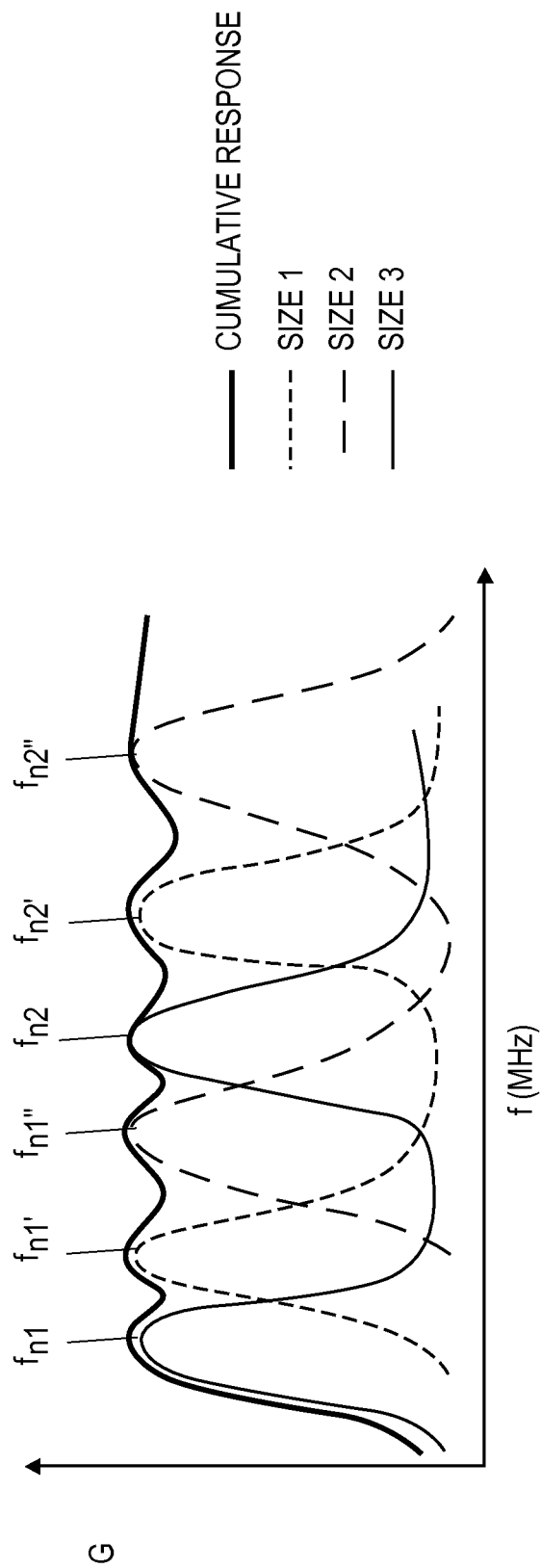
FIG. 5B is a plot of performance metrics for the PMUT array illustrated in FIG. 5A.

FIG. 5B is a plot of performance metrics for the PMUT array illustrated in FIG. 5A, having for example spheroidal piezoelectric membranes with diameters of size 1, size 2 and size 3. As shown in FIG. 5B, the spectral response includes six corresponding center frequency peaks as three pairs of peaks, $Fn_1$, $Fn_2$, $Fn_{1'}$, $Fn_{2'}$, $Fn_{1''}$, $Fn_{2''}$, with a cumulative response having a wide bandwidth (e.g., for 3 dB corner frequencies). Each pair of peaks, e.g., pairs $Fn_1$,$Fn_2$ and $Fn_{1'}$, $Fn_{2'}$ and $Fn_{1''}$, $Fn_{2''}$, represents first and second mode peaks of transducers of size 1, size 2, or size 3, respectively. The wider bandwidth for the pMUT array 500 is apparent when compared with that illustrated in FIGS. 4A/4B (for the pMUT array 100 having elements of a single size).

In an embodiment, the population of elements coupled to a same electrode rail and function together as a channel of the array, comprise a 2-D array of membranes. Thus, while the exemplary embodiments illustrated in FIGS. 1B and 5B include a single line of elements, such a line may be replicated a second dimension (e.g., x-dimension in FIG. 1B). A greater fill factor than that achieved by single file row embodiments may be achieved with such multiple rows, multiple columns per channel embodiments. As such, higher sensitivity may be possible.

Figure 6:
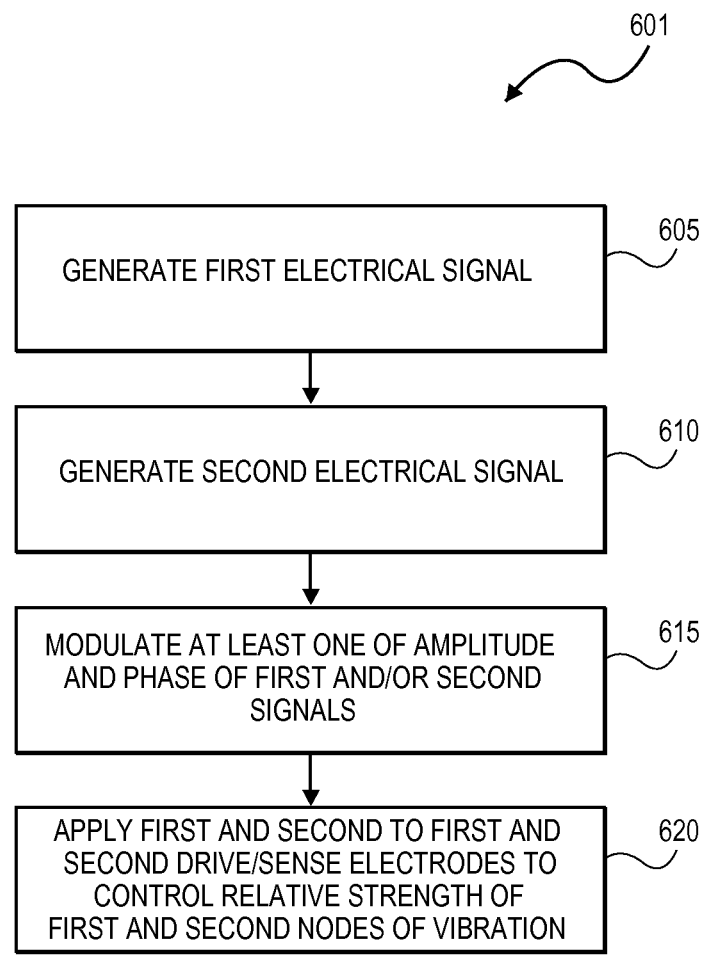
FIG. 6 is a flow diagram illustrating a portion of a method of operating an apparatus for generating and sensing pressure waves in a medium with a pMUT, in accordance with embodiments.

FIG. 6 is a flow diagram illustrating drive method for operating an apparatus for generating and sensing pressure waves in a medium with a pMUT, in accordance with embodiments.

Referring to operation 605, the driving portion of the method includes generating a first electrical signal. Referring to operation 610, a second electrical signal is also generated. Referring to operation 615, at least one of amplitude and phase of one of first and second signals is modulated relative to the other. Referring to operation 620, the first electrical signal is applied to the first drive/sense electrode of the pMUT and the second electrical signal to the second drive/sense electrode of the pMUT to control a relative strength of the first and second modes of vibration.

In an embodiment, referring again to the method described in association with FIG. 6, the first and second electrical signals are applied in phase to increase dominance of the first mode of vibration having a first frequency relative to a second mode of vibration. Alternatively, the first and second drive signals may be applied out of phase to increase the dominance of the second mode of vibration having a second frequency, higher than the first frequency.

Figure 7:
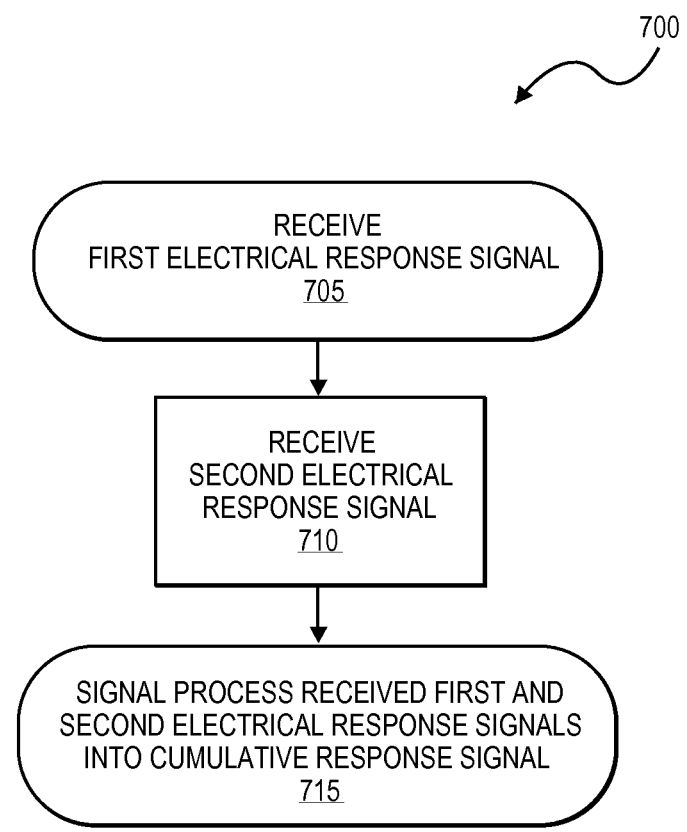
FIG. 7 is a flow diagram illustrating another portion of a method of operating an apparatus for generating and sensing pressure waves in a medium with a pMUT, in accordance with embodiments.

FIG. 7 is a flow diagram illustrating a sense method for operating an apparatus for generating and sensing pressure waves in a medium with a pMUT, in accordance with embodiments. At operation 705, a first electrical response signal is received from the first drive/sense electrode. At operation 710, a second electrical response signal is received from the second drive/sense electrode. At operation 715, any signal processing known in the art is performed on the first and second electrical response signals to generate a cumulative frequency response. For example, where the diameter of the piezoelectric membranes varies across one population of piezoelectric transducer elements, first and second electrical response signals are received for each diameter of the piezoelectric membrane are processed to provide a cumulative frequency response having a 3 dB bandwidth spanning between a lowest and highest center frequency associated with the first and second electrical response signals, respectively.

Figure 8:
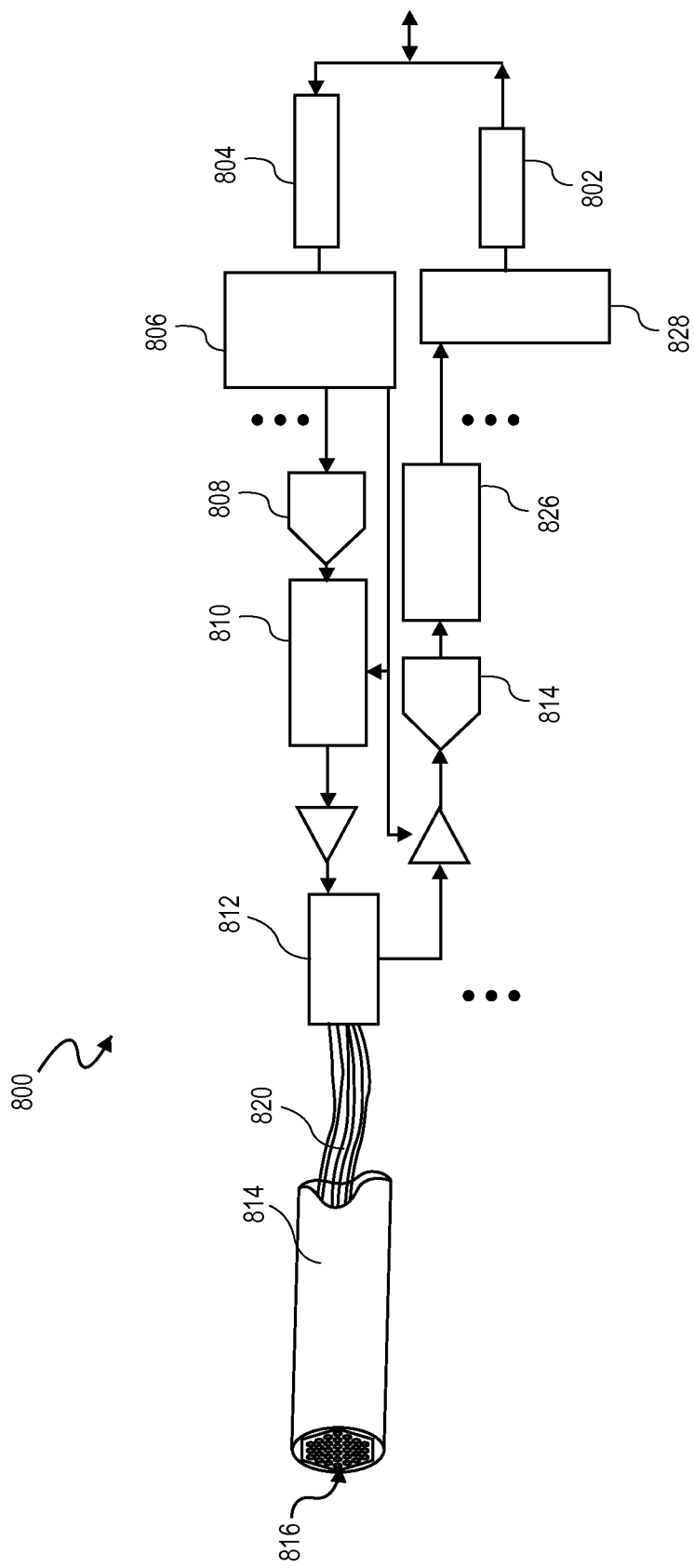
FIG. 8 is a functional block diagram of an ultrasonic transducer apparatus which employs a pMUT array, in accordance with an embodiment of the present invention.

FIG. 8 is a functional block diagram of an ultrasonic transducer apparatus 800 that employs a pMUT array, in accordance with an embodiment of the present invention. In an exemplary embodiment, the ultrasonic transducer apparatus 800 is for generating and sensing pressure waves in a medium, such as water, tissue matter, etc. The ultrasonic transducer apparatus 800 has many applications in which imaging of internal structural variations within a medium or multiple media is of interest, such as in medical diagnostics, product defect detection, etc. The apparatus 800 includes at least one pMUT array 816, which may be any of the pMUT arrays described elsewhere herein having any of the transducer element and element population attributes described. In exemplary embodiment, the pMUT array 816 is housed in a handle portion 814 which may be manipulated by machine or by a user of the apparatus 800 to change the facing direction and location of the outer surface of the pMUT array 816 as desired (e.g., facing the area(s) to be imaged). Electrical connector 820 electrically couple channels of the pMUT array 816 to a communication interface external to the handle portion 814.

In an embodiment, the apparatus 800 includes a signal generator, which may be any known in the art, coupled to the pMUT array 816, for example by way of electrical connector 820. The signal generator is to provide an electrical drive signal on two separate drive/sense electrodes for each transducer element in a population of elements. In one specific embodiment, the signal generator is to apply an electrical drive signal to cause the piezoelectric transducer element populations to resonate at frequencies between 10 MHz and 30 MHz in a first mode and between 20 and 60 MHz in a second mode. In an embodiment, the signal generator includes a de-serializer 804 to de-serialize control signals that are then de-multiplexed by demux 806. The exemplary signal generating means further includes a digital-to-analog converter (DAC) 808 to convert the digital control signals into driving voltage signals for the individual transducer element channels in the pMUT array 816. Respective time delays can be added to the individual drive voltage signals by a programmable time-delay controller 810 to alter vibratory modes of each transducer element and to modulate responses of separate element populations to beam steer, or create the desired beam shape, focus, and direction, etc. Coupled between the pMUT channel connector 802 and the signal generating means is a switch network 812 to switch the pMUT array 816 between drive and sense modes.

In an embodiment, the apparatus 800 includes a signal receiver, which may be any known in the art, coupled to the pMUT array 816, for example by way of electrical connector 820. The signal receiver is to receive an electrical sense signal from two drive/sense electrode channels for each transducer element in the pMUT array 816. In one embodiment of a signal receiver, a analog to digital converter (ADC) 814 is to receive voltages signals from two drive/sense electrode channels for each transducer and convert them to digital signals. The digital signals may then be stored to a memory (not depicted) or first passed to a signal processing means. An exemplary signal processing means includes a data compression unit 826 to compress the digital signals. A multiplexer 818 and a serializer 828 may further process the received signals before relaying them to a memory, other storage, or a downstream processor, such as an image processor that is to generate a graphical display based on the received signals.

It is to be understood that the above description is intended to be illustrative, and not restrictive. For example, while flow diagrams in the figures show a particular order of operations performed by certain embodiments of the invention, it should be understood that such order is not required (e.g., alternative embodiments may perform the operations in a different order, combine certain operations, overlap certain operations, etc.). Furthermore, many other embodiments will be apparent to those of skill in the art upon reading and understanding the above description. For example, it is to be understood the while the various embodiments described herein are all presented in the context of a pMUT, one or more of the structures or techniques disclosed may be applied to other types of ultrasonic transducer arrays and indeed even more generally to various other MEMs transducer arrays, for example those in inkjet technology. Thus, while a pMUT array is presented as a model embodiment for which certain synergies and attributes can be most clearly described, the disclosure herein has a far broader application. Thus, although the present invention has been described with reference to specific exemplary embodiments, it will be recognized that the invention is not limited to the embodiments described, but can be practiced with modification and alteration within the spirit and scope of the appended claims. The scope of the invention should, therefore, be determined with reference to the appended claims, along with the full scope of equivalents to which such claims are entitled.

What is claimed is:

1. A piezoelectric micromachined ultrasonic transducer (pMUT), comprising:
 a piezoelectric membrane disposed on a substrate;
 a reference electrode coupled to the membrane; and
 a first and second drive/sense electrode coupled to the membrane to drive or sense a first and second mode of vibration in the membrane;
wherein the piezoelectric membrane has a circular or spheroidal or ellipsoidal geometry and is anchored to the substrate at a perimeter of the membrane,
wherein the first drive/sense electrode has a circular or spheroidal geometry with a diameter smaller than that of the membrane and with a center aligned to a center of the membrane, and
wherein the second drive/sense electrode has an annular geometry with a center aligned to the center of the membrane, with an outer diameter that is smaller than that of the membrane and with an inner diameter that is greater than an outer diameter of the first drive/sense electrode to circumscribe at least a portion of the first drive electrode.

2. The pMUT of claim 1, wherein the membrane has rotational symmetry, the first and second drive/sense electrodes are co-planar and disposed on a first side of the piezoelectric membrane, and wherein the reference electrode is disposed on an opposite side of the piezoelectric membrane.

3. The pMUT of claim 2, wherein the second drive/sense electrode comprises a discontinuity through which a lead coupled to the first drive/sense electrode is routed.

4. The pMUT of claim 1, wherein the membrane diameter is larger than 2 μm, wherein first mode of vibration has a first resonant frequency of at least 40 MHz, and wherein the second mode of vibration has a second resonant frequency greater than that of the first resonant frequency.

5. A method of operating an apparatus for generating and sensing pressure waves in a medium with the pMUT of claim 1, the method comprising:
   generating a first electrical signal;
   generating a second electrical signal;
   modulating at least one of amplitude and phase of one of first and second signals relative to the other; and
   applying the first electrical signal to the first drive/sense electrode and the second electrical signal to the second drive/sense electrode to control a relative strength of the first and second modes of vibration.

6. The method of claim 5, wherein the first and second electrical signals are applied in phase to increase a strength of the first mode of vibration having a first frequency relative to a strength of the second mode of vibration, and wherein the first and second signals are applied out of phase to increase the strength of the second mode of vibration having a second frequency, higher than the first frequency, relative to the strength of the first mode of vibration.

7. The method of claim 5, further comprising:
   receiving a first electrical response signal from the first drive/sense electrode relative to the reference electrode;
   receiving a second electrical response signal from the second drive/sense electrode relative to the reference electrode; and
   signal processing the first and second electrical response signals to generate a cumulative frequency response.

8. The method of claim 7, wherein the diameter of the piezoelectric membrane varies across one population of piezoelectric transducer elements;
   wherein first and second electrical response signals are received for each diameter of the piezoelectric membrane; and
   wherein the cumulative frequency response has a continuous 3 dB bandwidth between a lowest and highest center frequency of the first and second electrical response signals.

9. An apparatus for generating and sensing pressure waves in a medium, the apparatus comprising:
   a piezoelectric micromachined ultrasonic transducer (pMUT) further comprising:
      a piezoelectric membrane disposed on a substrate;
      a reference electrode coupled to the membrane; and
      a first and second drive/sense electrode coupled to the membrane to drive or sense a first and second mode of vibration in the membrane;
   wherein the piezoelectric membrane has a circular or spheroidal geometry and is anchored to the substrate at a perimeter of the membrane,
   wherein the first drive/sense electrode has a circular or spheroidal geometry with a diameter smaller than that of the membrane and with a center aligned to a center of the membrane, and
   wherein the second drive/sense electrode has an annular geometry with a center aligned to the center of the membrane, with an outer diameter that is smaller than that of the membrane and with an inner diameter that is greater than an outer diameter of the first drive/sense electrode to circumscribe at least a portion of the first drive electrode;
   a first signal generator coupled to the first drive/sense electrode and to drive a first electrical signal on the first drive/sense electrode relative to the reference electrode; and
   a second signal generator coupled to the second drive/sense electrode and to drive a second electrical signal on the second drive/sense electrode relative to the reference electrode.

10. The apparatus of claim 9, wherein the first and second signal generators are to drive the first and second electrical signals in phase to excite a first resonant mode of the membrane more than a second resonant mode.

11. The apparatus of claim 9, wherein the first and second signal generators are to drive the first and second electrical signals out of phase to excite a second resonant mode of the membrane more than a first resonant mode, the second mode having a higher resonant frequency than that of the first resonant mode.

12. The apparatus of claim 9, further comprising a signal processor coupled to the first and second drive electrodes, the signal processor to receive both a low frequency component and a high frequency component of a spectrum in response to the membrane vibrating in the first and second modes.

13. A piezoelectric micromachined ultrasonic transducer (pMUT) array, comprising:
   a plurality of sets of electrode rails disposed over an area of a substrate, each set of electrode rails comprising a reference rail and a pair of independently electrically addressable drive/sense rails and;
   a plurality of piezoelectric transducer elements, the plurality comprising separate element populations, each element population including more than one transducer element coupled to one of the sets of electrode rails, wherein each of the piezoelectric transducer elements further comprises:
      a piezoelectric membrane;
      a reference electrode coupled to the membrane and the reference rail; and
      a first and second drive/sense electrode coupled to the membrane and to respective ones of the drive/sense rail pair;
   wherein the piezoelectric membrane has a circular or spheroidal geometry and is anchored to the substrate at a perimeter of the membrane,
   wherein the first drive/sense electrode has a circular or spheroidal geometry with a diameter smaller than that of the membrane and with a center aligned to a center of the membrane, and
   wherein the second drive/sense electrode has an annular geometry with a center aligned to the center of the membrane, with an outer diameter that is smaller than that of the membrane and with an inner diameter that is greater than an outer diameter of the first drive/sense electrode to circumscribe at least a portion of the first drive electrode.

14. The pMUT array of claim 13, wherein the diameter of the piezoelectric membrane varies across one population of piezoelectric transducer elements.

15. The pMUT array of claim 14, wherein a cumulative frequency response generated by one population has a continuous 3 dB bandwidth between a lowest and highest center frequency corresponding to first and second resonant modes of the transducers.

16. The pMUT array of claim 13, wherein the plurality of sets of electrode rails form a linear array of channels in a first dimension, and wherein transducers in an element population are aligned along a second dimension and along the first dimension to provide a 2D element array in each channel.

* * * * *